United States Patent
Steinhardt

(10) Patent No.: US 7,371,513 B2
(45) Date of Patent: *May 13, 2008

(54) METHOD OF PRESERVING CORNEAL TISSUE USING POLYOXYETHYLENE/POLYOXYPROPYLENE COPOLYMER

(75) Inventor: Richard A. Steinhardt, Berkeley, CA (US)

(73) Assignee: Regents of the University of California, Oakland, CA (US)

( * ) Notice: Subject to any disclaimer, the term of this patent is extended or adjusted under 35 U.S.C. 154(b) by 384 days.

This patent is subject to a terminal disclaimer.

(21) Appl. No.: 11/015,180

(22) Filed: Dec. 17, 2004

(65) Prior Publication Data

US 2005/0156378 A1    Jul. 21, 2005

Related U.S. Application Data

(63) Continuation-in-part of application No. 10/738,331, filed on Dec. 17, 2003, now Pat. No. 7,087,369.

(51) Int. Cl.
*A01N 1/00* (2006.01)
(52) U.S. Cl. ...................................................... 435/1.1
(58) Field of Classification Search ..................... None
See application file for complete search history.

(56) References Cited

U.S. PATENT DOCUMENTS 7,087,369 B2 * 8/2006 Steinhardt .................. 435/1.1

2007/0087320 A1 * 4/2007 Licari et al. ................. 435/1.1

FOREIGN PATENT DOCUMENTS

| WO | 2005-013690 | * | 2/2005 |
| WO | 2007008697 | * | 1/2007 |

OTHER PUBLICATIONS

Sato et al., "Effects of pulronic F68 on t-PA producing Chinese hamster ovary (CHO) cells under agitating and static conditions", Animal Cell Technology: Basic & Applied Aspects, Proceedings of the Annual Meeting of the Japanese Association for Animal Cell Technology, 15th, Fuchu, Japan, Nov. 11-15, 2002 (2003): 173-177. Kluwer Academic Publishers.*
Solberg et al., A New Protective Solution for Hypothermic Storage of Free Vein Grafts in Cardiovascular Surgery. Scand J Clin Lab Invest 1992, 52 (2), p. 73-82.
Cavallari et al., University of Wisconsin Solution Effects on Intimal Proliferation in Canine Autogenous Vein Grafts, J Surgical Res 1995, 59, p. 433-440.
Andrew et al., Comparison of Optixol and neomycin-Polymyxin B-Gramicidin Opthalmic Solution for Corneal Storage in the Dog. Veterinary Ophthalmol 1999, 2 (3) p. 155-161.

* cited by examiner

*Primary Examiner*—Sandra E. Saucier
(74) *Attorney, Agent, or Firm*—Richard Aron Osman

(57) ABSTRACT

Tissue preservation media comprising a polyoxyethylene/polyoxypropylene copolymer are used to preserve tissues and organs for storage and transplantation. In particular embodiments, the polyoxyethylene/polyoxypropylene copolymer is Pluronic F68 or FLOCOR (CRL-5861; purified poloxamer 188), and the medium is Steinhardt medium, polyoxyethylene/polyoxypropylene copolymer-supplemented Optisol GS or polyoxyethylene/polyoxypropylene copolymer-supplemented ViaSpan.

8 Claims, No Drawings

METHOD OF PRESERVING CORNEAL TISSUE USING POLYOXYETHYLENE/POLYOXYPROPYLENE COPOLYMER

CROSS-REFERENCE TO RELATED APPLICATION

This application is a continuation-in-part of Ser. No. 10/738,331, filed Dec. 17, 2003, now U.S. Pat. No. 7,087,369.

This work was supported by National Institutes of Health Grants AR44066 and EY 13436. The U.S. government may have rights in any patent issuing on this application.

FIELD OF THE INVENTION

The field of the invention is tissue preservation media.

BACKGROUND OF THE INVENTION

We have previously disclosed that the mechanism of cell membrane repair requires an active process of calcium regulated exocytosis (Steinhardt R A, Bi G, Alderton J M. *Cell Membrane Resealing by a Vesicular Mechanism Similar to Neurotransmission.* Science 1994; 263: 390-393). This lead to our idea that membrane breaks could be repaired by artificial means under conditions where normal metabolism is curtailed, such as the storage of donated tissues for transplantation.

We have devised new tissue preservation media, including corneal preservation media, and tested them against the American standard, Optisol GS (Bausch & Lomb). Optisol was developed for low temperature storage of corneas and other eye tissues by Richard L. Lindstrom and Debra Skelnik (U.S. Pat. Nos. 5,104,787; 5,407,669). This tissue preservation solution was originally marketed by Chiron Ophthalmics, Irvine, C A. Bausch & Lomb acquired Chiron Corp.'s vision-care product line in 1997. Optisol GS is commercially available from: Bausch & Lomb Surgical, Inc. (San Dimas, Calif.). Our media also outperform ViaSpan (Barr Laboratories, Pomona, N.Y.) in side-by-side tissue preservation studies.

Relevant Literature

Togo T, Alderton, J M, Bi G, Steinhardt R A. The mechanism of facilitated cell membrane resealing. Journal of Cell Science 1999; 112: 719-731; Togo T, Krasieva T B, Steinhardt R A. A Decrease in Membrane Tension Precedes Successful Cell-Membrane Repair. Molecular Biology of the Cell 2000; 11: 4339-4346; Bi G, Morris R L, Liao G, Alderton J M, Scholey J M, Steinhardt R A. Kinesin- and Myosin-driven Steps of Vesicle Recruitment for $Ca^{2+}$-regulated Exocytosis. The Journal of Cell Biology 1997; 138(5): 999-1008). Greenbaum A, Hasany S M, Rootman D. Optisol vs Dexsol as storage media for preservation of human corneal epithelium, Eye. 2004 May; 18(5):519-24' Peter H. Laverty, et al., A Preliminary Study of Intravenous Surfactants in Paraplegic Dogs: Polymer Therapy in Canine Clinical SCI, Journal of Neurotrauma December 2004, Vol. 21, No. 12: 1767-1777.

SUMMARY OF THE INVENTION

The invention provides methods and compositions for preserving tissues and organs, particularly corneal tissue, for storage and transplantation. The compositions include media comprising a polyoxyethylene/polyoxypropylene copolymer in an amount sufficient to increase tissue storage-ability, particularly concentrations of about 0.5 to 5 mg/ml. In particular embodiments, the polyoxyethylene/polyoxypropylene copolymer is Pluronic F68 or FLOCOR (CRL-5861; purified poloxamer 188), and the medium is Steinhardt medium, Optisol GS supplemented with the polyoxyethylene/polyoxypropylene copolymer, or ViaSpan supplemented with the polyoxyethylene/polyoxypropylene copolymer.

In other embodiments, the invention provides kits for preserving tissue including:

kits comprising a premeasured amount of a disclosed preservation medium;

kits comprising a premeasured amount of a disclosed preservation medium, and recorded instructions copackaged or associated with the premeasured amount describing use of the medium to preserve a tissue; and kits for making a disclosed medium comprising premeasured amounts of the ingredients, or a plurality of the ingredients; and recorded instructions copackaged or associated with the premeasured amounts describing how to combine the ingredients to make the medium.

The invention also provides methods of making a disclosed medium, comprising the step of combining the recited ingredients to make the medium; and methods of using a disclosed medium comprising incubating a tissue in the medium, preferably cornea tissue, preferably at 4 degrees C., and preferably for at least 7 days, typically not more than 21 days. The incubating step is typically followed by an assessment of post-incubation survival utility to determine whether the tissue has retained its suitability for its intended use, typically transplantation.

DESCRIPTION OF PARTICULAR EMBODIMENTS OF THE INVENTION

The invention provides methods and compositions for preserving tissues and organs, particularly transplantable tissues and organs including kidney, liver, pancreas, heart, lung, bone marrow, skin grafts, and particularly corneal tissue, for warm and cold storage and transplantation. The compositions include media comprising or supplemented with a polyoxyethylene/polyoxypropylene copolymer in an amount sufficient to increase tissue storage-ability, particularly concentrations of about 0.5 to 5 mg/ml. Tissue storage-ability may be measured by post-storage cell and tissue viability, transplantability, etc. In particular embodiments, the polyoxyethylene/polyoxypropylene copolymer is Pluronic F68 or FLOCOR (CRL-5861; purified poloxamer 188), and the medium is Steinhardt medium, Optisol GS supplemented with the polyoxyethylene/polyoxypropylene copolymer, or ViaSpan supplemented with the polyoxyethylene/polyoxypropylene copolymer.

Optisol GS and ViaSpan are commercially available products. Steinhardt medium is a tissue preservation medium based on fundamental physiological principles and on research findings from our laboratory regarding maintenance of cell membrane integrity. After testing many different iterations, we have established a particular formulation that provides exceptional tissue preservation of a panel of human and large animal organs and tissues, including cornea, kidney and heart tissue. The medium is typically provided in sterile solution; the ingredients and their final sterile solution concentrations are as follows:

potassium sulfate $K_2SO_4$ (5 mM)
L-aspartic acid (110 mM)
magnesium sulfate (1.2 mM)

calcium hydroxide (2.0 mM)
potassium phosphate monobasic $KH_2PO_4$ (20 mM)
N-2-hydroxyethylpiperazine-N'-2-ethanesulfonic acid (HEPES) (5 mM)
ethylenediaminetetraacetic acid (EDTA) (1 mM)
taurine (20 mM)
zinc sulfate (1 microM)
N-(tert-butyl) hydroxylamine HCL (200 microM)
dextran M.W. 60,00-90,000 (5.5% w/v)
N-acetyl-cysteine (0.5 mM)
gentamycin sulfate (0.02% w/v)
creatine phosphate (5 mM)
Lipid Concentrate (GIBCO/INVITROGEN #11905-031) (1% v/v) at pH adjusted to 7.45 with 1 M KOH, and having an osmolarity of 310 to 320 mOsmoles.

The ionic composition of Steinhardt medium is designed to approximate intracellular ionic composition for potassium, sodium, and magnesium ions.

The HEPES (SIGMA #H-9136)(N-2-Hydroxyehtylpiperazine-N'-2-ethanesulfonic acid) provides a physiologically compatible buffer widely used in cell culture media. The potassium salts of the sulfate ion ($K_2SO_4$) and the monobasic phosphate ion ($H_2PO_4$) are used in place of the sodium salts of these ions that are typically used in cell culture media.

L-aspartic acid is provided based on observations in our laboratory that cells microinjected with solutions containing high concentrations of the potassium salt of L-aspartic acid continue to grow and divide. L-aspartic acid is a key amino acid in cellular metabolism that links the urea cycle to the citric acid cycle. Steinhardt medium uses 110 millimolar L-aspartic acid to yield 110 millimolar aspartate. 13 millimolar aspartate has been used in cardioplegia (Rosenkranz et al., Journal of Thoracic Cardiovascular Surgery 1986; 91: 428-435).

Potassium hydroxide is used to adjust the pH, causes the acids such as L-aspartic acid and ethylenediaminetetraacetic acid (EDTA) to dissolve, and also provides high potassium ion levels characteristic of the intracellular environment.

The chelator ethylenediaminetetraacetic acid (EDTA) is used to buffer the level of calcium, magnesium, and zinc ions. Extracellular free calcium ion at about 1 millimolar and free magnesium ion at about 1.2 millimolar result in optimal cell membrane repair (Steinhardt R A, Bi G, Alderton J M. Cell Membrane Resealing by a Vesicular Mechanism Similar to Neurotransmission. Science 1994; 263: 390-393). This paper demonstrates that cell membrane repair is an active biological process that requires calcium-dependent exocytosis of vesicles at the cell membrane. Excessive free magnesium ion antagonizes the vesicle exocytosis and membrane resealing. EDTA also chelates trace amounts of iron and copper that may be present in the medium. Iron and copper are known to be catalytic for free radical reactions that are damaging to cells (Evans et al. Catalytic Metal Ions and the Loss of Reduced Glutathione from University of Wisconsin Preservation Solution. Transplantation 1996; 62(8): 1046-1049)

The zinc ion is an essential cofactor for DNA repair and other enzymatic cellular processes (Chimienti F, Aouffen M, Favier A, Seve M. Zinc homeostasis-regulating proteins: new drug targets for triggering cell fate. Current Drug Targets 2003; 4(4):323-38).

The amino acid taurine is cytoprotective (Eppler B, Dawson R Jr. Cytoprotective role of taurine in a renal epithelial cell culture model. Biochemical Pharmacology 2002; 63: 1051-1060). It is an abundant intracellular amino acid and provides multiple homeostatic functions (Lourenco et al., Taurine: a conditionally essential amino acid in humans? An overview in health and disease. Nutr Hosp. 2002;17(6):262-70).

The 5.5% dextran is consistent with the corneal preservation medium described by McCarey B E and Kaufinan H E. Improved Corneal Storage. Investigative Ophthamology 1974; 13(3): 165-173; and U.S. Pat. No. 5,370,989. Optisol GS contains 1% dextran. The dextran used has an average molecular weight between 64,000 and 76,000.

The N-acetyl-cysteine is a cell permeable precursor of glutathione. (Ceconi C, Curello S, Cargnoni A, Ferrari R, Albertini A, Visioli O. The role of glutathione status in the protection against ischemic and reperfusion damage: effects of N-acetyl cysteine. Journal of Molecular and Cellular Cardiology 1988; 20(1): 5-13). The 0.5 mM concentration is consistent with that used in U.S. Pat. No. 5,370,989.

N-tert-Butyl hydroxylamine is an antioxidant that prevents free radical-induced toxicity to mitochondria (Liu J, Atamna H, Kuratsune H, Ames B N. *Delaying brain mitochondrial decay and aging with mitochondrial antioxidants and metabolites.* Ann N Y Acad Sci. 2002; 959:133-66). Also, Atamna et al. *N-t-Butyl hydroxylamine is an antioxidant that reverses age-related changes in mitochondria in vivo and in vitro.* FASEB J 2001;15(12):2196-204; also, U.S. Pat. No. 6,455,589. N-t-butyl hydroxylamine, a hydrolysis product of alpha-phenyl-N-t-butyl nitrone, is more potent in delaying senescence in human lung fibroblasts. J Biol Chem. 2000; 10;275(10):6741-8.

The Lipid Concentrate (GIBCO/INVITROGEN catalog number 11905-031) is formulated for use in suspension cultured cells grown for recombinant protein production, and allows for serum-free growth that facilitates purification of the secreted recombinant protein. An ingredient in the Concentrate is Pluronic F68 (BASF, Ludwigshafen, Germany; also called Poloxamer 188 and Lutrol F68, RheothRx, (Glaxo) and Flocor (CytRx)), a non-ionic surfactant included by GIBCO to help dissolve the lipids.

Pluronic F68 also provides a beneficial effect on cell survival in suspension culture (Kilburn D G, Webb F C. The Cultivation of Animal Cells at Controlled Dissolved Oxygen Partial Pressure. Biotechnology and Bioengineering 1968; 10: 801-814), and has been used to protect animal cells from damage caused by shear and the effects of sparging (the aeration bubbles used in bioreactors; Hua et al., Critical Reviews in Biotechnology 1993; 13(4): 305-28). Its use has also been proposed as an intravenous agent for treatment of sickle cell disease and acute vaso-occlusive disorders, and to preserve organs for transplantation (e.g. U.S. Pat. No. 5,990,241).

Pluronic F68 is a mixture of polyoxyethylene and polyoxypropylene; commercial preparations are mixtures of the polymers with a range of molecular weight from 7680 to 9510. See BASF Technical Bulletin "Pluronic Block Copolymer NF Grades (Poloxamer NF Grades)." U.S. Pat. No. 6,359,014 describes one purification method for commercial preparations of Pluronic F68. FLOCOR (CRL-5861; purified poloxamer 188; CytRx Corporation, Los Angeles, Calif.) is another purified form of Pluronic F68; see, e.g. WO9216484; U.S. Pat. No. 5,990,241; Moghimi S M, et al., 2004, Biochim Biophys Acta, 1689(2):103-13.

The subject media may also be used to improve organ transplantation success by perfusing the organ before surgical removal from the donor. This timing is important because we have previously shown that cell membranes must be repaired within 30-90 seconds for a cell to survive a disruption of this protective interface (Steinhardt R A, Bi G, Alderton J M. Cell Membrane Resealing by a Vesicular Mechanism Similar to Neurotransmission. Science 1994; 263: 390-393).

The invention provides methods of making and using the subject media, and various kits for making and using the subject media. Methods of making a disclosed medium include methods comprising combining the recited ingredients to make the medium; and methods of using a disclosed medium include methods comprising incubating a tissue in the medium, preferably cornea tissue, preferably at 4 degrees C., and preferably for up to at least about 7 days, typically not more than about 21 days.

Kits for using the subject media include kits comprising a premeasured amount of the disclosed medium; kits comprising a premeasured amount of a disclosed medium and instructions copackaged or associated with the premeasured amount describing use of the medium to preserve a tissue in the medium, preferably cornea tissue, preferably at 4 degrees C., and preferably for up to at least about 7 days, typically not more than about 21 days. Preferred instructions disclose that a subject medium can provide, or has been shown to provide cold cornea tissue storage for at least about 7 days, preferably for up to about 21 days. The premeasured amounts are preferably contained in a container labeled with the instructions.

Kits for making a disclosed medium include kits comprising premeasured amounts of the recited ingredients, one or more of the ingredients, or a plurality of the ingredients, and recorded instructions copackaged or associated with the premeasured amounts describing the medium and/or how to combine the ingredients to make the medium. The premeasured amounts are preferably contained in a container labeled with the instructions.

EXAMPLES

Evaluations of the endothelial cell layer in bovine corneas in different media. post-incubation survival utility or usefulness for transplantation is defined as less than 3% dying and less than 1.5% missing. Missing cells leave a gap in the layer; calcein-AM staining for esterase activity is used to determine cell health. Transplant surgeons typically use missing cell counts and morphology alone as the index of health and post-incubation survival utility.

TABLE I

Corneas stored in Optisol at 4° C. All experiments were performed double-blind.
Conclusion: Optisol does not provide useful tissue beyond 6 days cold storage.

| Days at 4° C. | Percent live | percent dying | percent missing | total cells examined |
|---|---|---|---|---|
| 6 | 98.0 | 2.0 | 0.0 | 892 |
| 6 | 98.6 | 1.0 | 0.3 | 937 |
| 9 | 88.6 | 5.4 | 6.0 | 1338 |
| 9 | 82.3 | 11.6 | 6.1 | 1386 |
| 12 | 67.1 | 16.5 | 16.3 | 1393 |
| 12 | 70.7 | 16.4 | 12.9 | 566 |

TABLE II

Comparison of Steinhardt medium with a defined composition Optisol medium. Corneas stored at 4° C. in Optisol(F) defined media (1) vs. Steinhardt medium.
Conclusion: Steinhardt medium stored corneas retain utility at least 21 days.

| Days at 4° C. | Medium | Percent Live | Percent Dying | Percent Missing | Total cells examined |
|---|---|---|---|---|---|
| 4 | Steinhardt | 99.4 (1083) | 0.6 (7) | 0 | 1090 |
| 4 | Steinhardt | 100 (776) | 0 | 0 | 776 |
| 4 | Optisol(F) | 99.0 (576) | 1.0 (6) | 0 | 582 |
| 4 | Optisol(F) | 95.0 (623) | 3.4 (22) | 1.7 (11) | 656 |
| 10 | Steinhardt | 97.8 (840) | 2.0 (17) | 0.2 (2) | 859 |
| 10 | Steinhardt | 100 (635) | 0 | 0 | 635 |
| 10 | Optisol(F) | 92.6 (598) | 5.9 (38) | 1.5 (10) | 646 |
| 10 | Optisol(F) | 91.0 (1154) | 4.9 (62) | 4.1 (52) | 1268 |
| 14 | Steinhardt | 98.7 (869) | 0.9 (8) | 0.4 (3) | 880 |
| 14 | Steinhardt | 99.3 (1216) | 0.7 (9) | 0 | 1225 |
| 14 | Optisol(F) | 85.3 (1039) | 8.4 (102) | 6.3 (77) | 1218 |
| 14 | Optisol(F) | 93.3 (1228) | 4.0 (52) | 2.7 (35) | 1315 |
| 21 | Steinhardt | 96.4 (888) | 2.6 (24) | 1.0 (9) | 921 |
| 21 | Steinhardt | 97.8 (1271) | 1.6 (21) | 0.6 (8) | 1300 |
| 21 | Optisol(F) | 63.6 (743) | 13.5 (158) | 22.9 (268) | 1169 |
| 21 | Optisol(F) | 66.7 (933) | 17.2 (241) | 16.1 (225) | 1399 |

(1) Optisol(F) is formulated as commercial Optisol, but is freshly made and provides better results than commercial Optisol after several days of cornea storage.

Formulation I: Steinhardt Cornea Preservation Medium

| RT Ingredients | Manufacturer | [ ] | MW | for 200 ml |
|---|---|---|---|---|
| Potassium Sulfate $K_2SO_4$ | Mallinckrodt | 5 mM | 174.26 | 0.174 g |
| L-Aspartic Acid | Sigma A-7219 | 110 mM | 133.10 | 2.93 g |
| Magnesium Sulfate | Sigma —1880 | 1.2 mM (1) | 246.5 | 59 mg |
| Calcium Hydroxide | Allied Chemical | 2.0 mM (2) | 74.1 | 29.6 mg |
| Potassium Phosphate, Monobasic $KH_2PO_4$ | Mallinckrodt | 20 mM | 136.1 | 0.544 g |
| HEPES | Sigma H-9136 | 5 mM | 238.3 | 0.238 g |
| EDTA | Sigma EDS | 1 mM | 292.2 | 58.44 mg |
| Taurine | Sigma T-8691 | 20 mM | 125.1 | 0.50 g |

TABLE II-continued

| | | | | |
|---|---|---|---|---|
| Zinc Sulfate | Allied Chemical | 1 μM (3) | 287.54 | 200 μl of 2.88 mg/10 ml |

(1) free $Mg^{2+}$: 1.2 mM at 4 C.; 1.17 mM at 36 C.
(2) free $Ca^{2+}$: 1 mM at 36 C.
(3) free zinc: $1.4 \times 10^{-12}$ M at 36 C.; $1.7 \times 10^{-12}$ M at 4 C.; stock is 1 mM (1000×)
Adjust to about pH 7.4 using 1 M KOH.
Add 1 M KOH slowly to dissolve the salts completely.

| | | | | |
|---|---|---|---|---|
| N-(tert-Butyl) hydroxylamine HCL | Aldrich 19,475-1 | 200 μM | 125.6 | 5 mg |

Refrigerator ingredients:

| | | | | |
|---|---|---|---|---|
| Dextran | Sigma D-4751(4) | 5% | 68,800 | 10 g |
| N-acetyl-cysteine | Sigma A-9165 | 0.5 mM | 163.2 | 16.3 mg |
| Gentamycin Sulfate | Biowhittaker | | | 20 mg |

Freezer ingredient:

| | | | | |
|---|---|---|---|---|
| Creatine Phosphate | Calbiochem 2380 | 5 mM | 255.1 | 0.255 g |

(4) Takes about 1 hr. to dissolve at RT with stirring
Adjust volume to 190 ml. Adjust pH to 7.45. Bring volume to 200 ml. Check osmolarity. = 314 mOsmoles. Filter sterilize 0.2μ
Add 1 ml lipid concentrate (Gibco 11905-031(5))/100 ml medium after the medium is aliquoted into the corneal storage vials.
(5) Lipid Concentrate Composition: 100×
Arachidonic Acid 2 mg/liter
Cholesterol 0.22 g/liter
DL-alpha-Tocopherol Acetate 70 mg/liter
Linoleic, Linolenic, Myristic, Oleic, Palmitoleic, Stearic, and Palmitic Acids All 10 mg/liter
Pluronic F-68 100 g/liter
Tween 80 2.2 g/liter Formulation II: Optisol(F) Medium

| Ingredient; storage. | Source | Quantity |
|---|---|---|
| Medium 199, with Earle's salts, with L-glutamine, with 2,200 mg/L sodium bicarbonate, with 25 mM HEPES; 4 C. | GIBCO 12340-030 | 490 ml |
| Chondroitin sulfate A, sodium salt from bovine trachea; RT. | Calbiochem #230687 | 12.5 g/500 ml |
| Dextran, clinical grade. Av. MW 64.76K; 4 C. and desiccated. | Sigma D-4751 | 5 g/500 ml |

Stir and intermittently shake the above ingredients at RT and protect from light for several hours or until solids are dissolved. Then add:

| | | |
|---|---|---|
| Choline, Chloride salt; RT. | Sigma C-1879 | 0.5 mg/500 ml |
| Folic acid; RT. | Sigma F-8758 | 0.5 mg/500 ml |
| i-Inositol myo-inositol; RT. | Sigma I-7508 | 1 mg/500 ml |
| Inosine; RT. | Sigma I-4125 | 5 mg/500 ml |
| L-Asparagine; RT, desiccated. | Aldrich #A9, 300-3 | 6.6 mg/500 ml |
| Riboflavin; RT. | Sigma R-4500 | 0.05 mg/500 ml |
| Nicotinamide; RT. | Sigma —0636 | 0.5 mg/500 ml |
| L-glutamine; RT. | Sigma G-3126 | 100 mg additional/500 ml |
| Vitamin $B_{12}$; 4 C. and desiccated. | Sigma V-6629 | 0.68 mg/500 ml |
| D-Pantothenic acid; 4 C. and desiccated. | Sigma P-5155 | 0.5 mg/500 ml |
| Adenosine, free base 4 C. and desiccated. | Sigma A-9251 | 0.75 mg/500 ml |
| Alpha-tocopherol phosphate, disodium salt; 4C and desiccated. | Sigma T-2020 | 25 mg/500 ml |
| Pyridoxal HCl; −20 C. and desiccated. | Sigma P-9130 | 0.5 mg/500 ml |
| Gentamycin sulfate; 4 C. liquid stock @ 50 mg/ml | BioWhittaker # 17-518Z | 50 mg/500 ml |
| Sodium pyruvate liquid; 4 C. and protected from light; yields 1 mM final concentration. | GIBCO #11360-070 | 5 ml stock/500 ml |
| 2-mercaptoethanol liquid stock; 4 C. | GIBCO BRL #21985-023 | 0.45 ml/500 ml 1 microliter/ml |
| Thiamine, HCl Sigma T-1270; rapidly destroyed above pH 5.5; 1000× stock in MES = 2[N-Morpholino] ethane Sulfonic Acid buffer Sigma —8250, pH 5.5. Yields 0.5 mg Thiamine, HCl/500 ml Add just before cornea is placed in the medium. | | |

In another series of demonstrations, the preservation solutions, Steinhardt Medium and Optisol-like Medium were made using the ingredients in Formulation I and III, respectively. Initial experiments used dextran from *Leuconostoc mesenteroides* of average molecular weight of 64,000-76,000 (Sigma D 4751). Data from these experiments are shown in Table 4. The source of the dextran used for Steinhardt Medium in Table 3 was Amersham Biosciences (Catalog #US14495, Lot 108318, average molecular weight 60,000-90,000). Optisol-GS™ was purchased from Bausch & Lomb Surgical, Inc., San Dimas, Calif.

Bovine eyes were obtained from Rancho Veal, Petaluma, Calif. Two to 3 hours elapsed between death of the cattle and excision of the cornea with a 1 to 2 millimeter (mm) scleral rim from the enucleated eyes. During the approximately 80 min. transit time, 12 bovine eyes were packaged without medium in a plastic bag that rested on bubble paper above crushed ice in a styrofoam box. (Submersing the corneas in cold Ringer's during transport did not improve the endothelial preservation). The bovine corneas were dissected in a sterile laminar flow biological cabinet and then transferred to the corneal preservation media at 22° C. Each cornea was transferred with the epithelial side down to an ultraviolet light-sterilized Nalgene polycarbonate screw-capped jar #2116-0015 (Nalge Nunc International, Rochester, N.Y.) filled with 22 ml of medium. Corneas in the preservation media were then stored in a refrigerator for 3 to 21 days before being assayed for endothelial cell viability.

The viability of the corneal endothelium was quantified with the vital stain Calcein AM (Molecular Probes, Eugene, Oreg.). The hydrophobic and non-fluorescent Calcein AM readily diffuses across the plasma membrane and into the cytoplasm. In the cytoplasm, the AM moiety is hydrolyzed by cellular esterases to release the highly fluorescent Calcein. Live cells exhibit a bright green fluorescence with an especially bright nucleus. The bright nuclei are easily counted. Dead cells are dark, and dying cells are pale green. Calcein AM was purchased in 50 microgram aliquots. An aliquot was freshly mixed with cell culture-tested dimethylsulfoxide (DMSO, Sigma D2650, Sigma-Aldrich, St. Louis, Mo.) to yield a 4 millimolar (mM) Calcein AM stock. To aid dispersion of the hydrophobic Calcein AM in the Ringer's solution, 1 microliter (µl) of the Calcein stock was thoroughly mixed with 1 µl of Pluronic F-127 solution (25%, weight to weight, in DMSO). Pluronic F-127 was from Molecular Probes. This mixture was thoroughly mixed with 2 ml Ringer's in a 35 mm diameter Corning # 430165 petri dish (Corning, N.Y.). The cornea was gently transferred, epithelial side down, in the tipped petri dish to ensure that the Calcein AM in Ringer's covered the endothelial layer. The Ringer's was 138 mM Sodium Chloride; 2.7 mM Potassium Chloride; 12.4 mM 4-(2-hydroxyethyl)-1-piperazineethanesulfonic acid (HEPES); 5.6 mM D-glucose (dextrose); 1.06 mM Magnesium Chloride; 1.8 mM Calcium Chloride, pH 7.25 with Sodium Hydroxide (all salts from Sigma). The half cornea in Calcein AM Ringer's was placed in a 36° C. incubator for 1 hour. The half cornea was then carefully transferred, endothelial side down, to a 24×60 mm number one coverglass. A Zeiss IM-35 inverted fluorescence microscope (Thornwood, N.Y.) equipped with excitation and emission filters for Green Fluorescent Protein (filter set XF100-2 from Omega Optical, Brattleboro, Vt.) was used to illuminate the half cornea. The lens used was a Fluor 10 0.5 160/0.17 10× (Nikon, Melville, N.Y.). The central endothelial layer was photographed using a Nikon Coolpix 5000 digital camera with 3× optical zoom. 8 by 11 inch images were printed using a S900 color printer (Canon, Lake Success, N.Y.).

For analysis, each photograph was overlaid with a sheet of transparency film. A felt-tip lab pen was used to mark cells as they were counted and scored as bright (live), dim (dying), or dark (dead or missing). Dark areas were outlined. Later these dark, outlined areas were placed over normal, bright areas so that the number of missing cells could be estimated by counting the bright nuclei encompassed by the outline. The percentages of cells in each category were used to compare endothelial viability among preservation media.

Bovine corneas stored in a new experimental cold-preservation solution, Steinhardt Medium, show enhanced long-term viability of the endothelial cell layer compared to corneas stored in Optisol-GS™ Medium (Table 3). After 4 days at 4° C., the corneal endothelial qualitative viability is similar for corneas stored in Steinhardt Medium or in Optisol-GS™. After 14 days at 4° C., we found that that dead and dying cells are present in corneas preserved in Optisol-GS™, but virtually absent from corneas stored in Steinhardt Medium. By 21 days, corneas stored in Optisol-GS™ show conspicuous cell loss and a high percent of pale green dying cells. In contrast, corneas stored in Steinhardt Medium for 21 days at 4° C. show very few dead or dying cells. Black areas that are smaller than the diameter of an endothelial cell were probably created when adjacent cells repaired their cell membrane following mechanical damage.

A progressive and significant advantage for Steinhardt Medium over Optisol-GS™ Medium is seen (Table 3) when large numbers of cells in many corneas are scored as live, dying or missing (dead). A large advantage for Steinhardt Medium over Optisol-GS™ Medium is seen for corneas stored longer than 4 days. The percent viability is 99.7 in Steinhardt Medium versus 98.5% in Optisol-GS™ Medium after 4 days at 4° C. By 10 days in the different storage media, corneas in Steinhardt Medium have an endothelial viability of 98.9% while corneas stored in Optisol-GS™ Medium have only 93.5% viability. At 14 days, corneas stored in Steinhardt Medium still retain an average high endothelial cell viability of 98.5% while Optisol-GS™-stored corneas have an average endothelial cell viability of 86.9%. Finally, corneas stored in Steinhardt Medium for 21 days average 96.3% endothelial cell viability compared to about 67.9% endothelial viability for corneas stored in Optisol-GS™ Medium.

The advantage of Steinhardt Medium over Optisol-GS™ may be largely due to the addition of Pluronic F68 (Poloxamer 188). This non-ionic surfactant facilitates the resealing of disrupted membranes in the absence of normal mechanisms of cell membrane repair (Togo et al. 1999). In order to compare the effect of Pluronic F68 on endothelial membrane resealing at 4° C., we used a completely defined medium that is similar to Optisol-GS™. This Optisol-like Medium was composed using the published patent literature (U.S. Pat. No. 5,104,787). Optisol-GS™ may contain proprietary ingredients that are undisclosed in the patent literature so we chose to work with a defined solution for this direct comparison of the effects of pluronic. A higher level of endothelial cell viability was maintained in the corneas stored in the defined medium with Pluronic F68 (Table 4). After 3 days at 4° C. in the Optisol-like Medium, the corneas stored in both the medium plus Pluronic F68 and the medium without Pluronic F68 were equally viable (98.8% vs 98.7%). A large difference in endothelial cell viability was evident after 6 days storage at 4° C.: the endothelial cell viability in the Optisol-like Medium plus Pluronic F68 was 99.0% compared to 93.2% for corneas stored in the Optisol-like Medium without Pluronic F68. The inclusion of Pluronic F68 in the preservation medium continued to maintain endothelial cell viability for corneas stored for 18 days at 4° C. (97.7% viable). In contrast, corneas stored for 18 days at 4° C. in an Optisol-like Medium without Pluronic F68 showed only 79.9% viability. Optisol-like Medium appears to be as good as or better than Optisol-GS™ and the addition of pluronic has a large positive effect on endothelial viability.

The solvent used to dissolve Pluronic F68 was dimethylsulfoxide (DMSO) at 0.5%. DMSO has been shown to have a beneficial effect on cell survival in some systems, but had no effect on corneal endothelial cell survival in our experiments using bovine corneas. Corneas stored for 10 days in an Optisol-like Medium without Pluronic F68, but with 0.5% DMSO, showed a similar loss in endothelial cell viability (90.3% viability with DMSO vs 90.1% viabilty without DMSO).

| Formulation III: Optisol-like Medium | |
|---|---|
| Ingredient (source) | quantity/liter |
| Medium 199 (GIBCO 12340-030), with Earle's salts, with L-glutamine, with 2,200 mg/L sodium bicarbonate, with 25 mM HEPES. | 980 ml |
| Chondroitin sulfate A, sodium salt (Calbiochem # 230687) from bovine trachea. | 25 g |
| Dextran, clinical grade. Av. MW 64.76K (Sigma D-4751). | 10 g |
| Stir the above ingredients at RT and protected from light until solids are dissolved. Then add: | |
| Choline, Chloride salt (Sigma C-1879). | 1 mg |
| Folic acid (Sigma F-8758). | 1 mg |
| i-Inositol (myo-inositol) (Sigma I-7508). | 2 mg |
| Inosine (Sigma I-4125). | 10 mg |
| L-Asparagine (Aldrich #A9, 300-3). | 13.2 mg |
| Riboflavin (Sigma R-4500). | 0.1 mg |
| Nicotinamide (Sigma N-0636). | 1 mg |
| L-glutamine (Sigma G-3126). | 200 mg |
| Vitamin $B_{12}$ (Sigma V-6629). | 1.36 mg |
| D-Pantothenic acid (Sigma P-5155). | 1 mg |
| Adenosine, free base (Sigma A-9251). | 1.5 mg |
| Alpha-tocopherol phosphate, disodium salt (Sigma T-2020). | 50 mg |
| Pyridoxal HCl (Sigma P-9130). | 1 mg |
| Gentamycin sulfate (BioWhittaker # 17-518Z) stock @ 50 mg/ml. | 100 mg |
| Sodium pyruvate liquid (GIBCO #11360-070), 1 mM final concentration. | 10 ml |
| 2-mercaptoethanol liquid (GIBCO BRL #21985-023). | 0.9 ml |
| Thiamine, HCl (Sigma T-1270); 1000× stock in 2[N-Morpholino] ethane Sulfonic Acid buffer (Sigma M-8250), pH 5.5*. Add the above thiamine stock to the medium in the corneal storage vial at 1 microliter/ml Just before the cornea is placed in the medium. | 1 mg |

*Thiamine is rapidly destroyed in solutions above pH 5.5.

TABLE 3

Corneal Endothelial Viability

| Days at 4 C. | Medium | Percent Live | Percent Dying | Percent Missing |
|---|---|---|---|---|
| 4 | Steinhardt | 99.7 +/− 0.14* | 0.26 +/− 0.13* | 0.02 +/− 0.02 |
| 4 | Optisol | 98.5 +/− 0.42* | 1.12 +/− 0.25* | 0.42 +/− 0.28 |
| 10 | Steinhardt | 98.9 +/− 0.40* | 0.90 +/− 0.36** | 0.20 +/− 0.16* |
| 10 | Optisol | 93.5 +/− 1.14* | 4.12 +/− 0.50** | 2.32 +/− 0.49* |
| 14 | Steinhardt | 98.5 +/− 0.29* | 1.12 +/− 0.23** | 0.42 +/− 0.16** |
| 14 | Optisol | 86.9 +/− 2.15* | 7.56 +/− 0.93** | 5.52 +/− 0.80** |
| 21 | Steinhardt | 96.3 +/− 0.61* | 2.68 +/− 0.45* | 1.00 +/− 0.16* |
| 21 | Optisol | 67.9 +/− 1.38* | 11.12 +/− 2.03* | 20.92 +/− 1.49* |

Viability was assessed by the accumulation of fluorescent Calcein in the corneal endothelial cells. Live cells were bright green with bright nuclei. Dying cells were pale. Missing cells were dark. Four or five bovine corneas were assayed for each medium at each preservation time. A total of 41,657 central corneal endothelial cells were scored. The statistical analysis software was InStat 2.0 from GraphPad.com.
*indicates significant difference between Optisol and Steinhardt media ($P < 0.05$).
**indicates very significant difference between Optisol and Steinhardt media ($P < 0.01$).

TABLE 4

The effect of 1 mg/ml Pluronic F68 on corneal endothelial viability.

| Days at 4° C. | Pluronic F68 | Percent Live | Percent Dying | Percent Missing | Total Cells Examined |
|---|---|---|---|---|---|
| 3 | plus | 98.8 | 1.2 | 0 | 2496 |
| 3 | minus | 98.7 | 1.3 | 0 | 2479 |
| 6 | plus | 99.0 | 1.0 | 0 | 2424 |
| 6 | minus | 93.2 | 4.2 | 2.6 | 2852 |
| 9 | plus | 98.6 | 1.2 | 0.2 | 2885 |
| 9 | minus | 79.4 | 17.8 | 2.8 | 3467 |
| 12 | plus | 98.9 | 1.1 | 0.1 | 3385 |
| 12 | minus | 80.8 | 9.0 | 10.2 | 3605 |
| 18 | plus | 97.7 | 0.6 | 1.7 | 3107 |
| 18 | minus | 79.7 | 7.1 | 13.2 | 3333 |

Bovine corneas were stored at 4 C in Optisol-like defined media. These experiments were done double blind. Calcein accumulation was used to classify cells as live, dying, or missing. Cell counts are pooled from 3 corneas for each treatment, except for 18 days, which are from 2 corneas.

| Formulation IV. ViaSpan (Barr Laboratories, Pomona, NY) | | |
|---|---|---|
| Component | Concentration | Function |
| Raffinose | 30 mM (17.83 g/L) | Impermeant: suppression of hypothermic cell swelling |
| Lactobionic acid | 100 mM (35.83 g/L) | Impermeant: suppression of hypothermic cell swelling |
| Pentafraction (hydroxyethyl starch) | 50 g/L | Colloid: reduction of interstitial edema and endothelial cell swelling |
| Glutathione | 3 mM (0.992 g/L) | Antioxidant |
| Allopurinol | 1 mM (0.136 g/L) | Inhibition of xanthine oxidase activity and purine metabolism/reduction of oxygen free radicals |
| Adenosine | 5 mM (1.34 g/L) | Restoration of high energy phosphate |
| Potassium phosphate | 25 mM (3.4 g/L) | pH buffer: maintenance of intracellular sodium and potassium concentrations: restoration of high energy phosphate |
| Magnesium sulfate | 5 mM (1.23 g/L) | Preservation of intracellular magnesium concentration |
| Potassium hydroxide | 100 mM (5.61 g/L) | Maintenance of intracellular sodium and potassium concentrations |

-continued

Formulation IV. ViaSpan (Barr Laboratories, Pomona, NY)

| Component | Concentration | Function |
|---|---|---|
| Sodium hydroxide | 27 mM | Maintenance of intracellular sodium and potassium concentrations |

Solution is pH adjusted to 7.4 with either sodium hydroxide or hydrochloric acid. Final: Sodium=29 mM; Potassium=125 mM; mOsm/L=320+10 Immediately prior to use, to formulate the final solution, aseptically add: Penicillin G 200,000 units, regular insulin 40 units, and dexamethasone 16 mg.

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of preserving tissue, comprising the step of: incubating a tissue in a tissue preservation medium at 4 degrees C. for between 7 and 21 days, the medium containing a polyoxyethylene/polyoxypropylene copolymer in final concentration of 0.5 to 5 mg/ml, and the tissue is cornea tissue.

2. The method of claim 1 wherein the polyoxyethylene/polyoxypropylene copolymer is FLOCOR (CRL-5861; purified poloxamer 188).

3. The method of claim 1 wherein the polyoxyethylene/polyoxypropylene copolymer is Pluronic F68.

4. The method of claim 1 wherein the medium is Steinhardt mediums.

5. The method of claim 1 wherein the medium is Optisol GS supplemented with the polyoxyethylene/polyoxypropylene copolymer.

6. The method of claim 1 wherein the medium is ViaSpan supplemented with the polyoxyethylene/polyoxypropylene copolymer.

7. The method of claim 1 further comprising the step of verifying post-incubation survival and transplant utility of the tissue.

8. The method of claim 1 wherein the polyoxyethylene/polyoxypropylene copolymer is Pluronic F68, and the final concentration is 1 mg/ml.

* * * * *